US005672698A

United States Patent [19]

Chen et al.

[11] Patent Number: 5,672,698
[45] Date of Patent: Sep. 30, 1997

[54] PREPARATION OF 2',3'-DIDEHYDRO-3'-DEOXYTHYMIDINE FROM 5-METHYLURIDINE

[75] Inventors: Bang-Chi Chen, Manilus; Derron Ray Stark, Syracuse; Stephen Richard Baker, Cicero; Sandra L. Quinlan, Manlius, all of N.Y.

[73] Assignee: Bristol-Myers Squibb Co., New York, N.Y.

[21] Appl. No.: 309,637

[22] Filed: Sep. 23, 1994

Related U.S. Application Data

[63] Continuation-in-part of Ser. No. 153,058, Nov. 15, 1993, abandoned, and Ser. No. 152,778, Nov. 15, 1993, abandoned.

[51] Int. Cl.$^6$ .............................. C07H 1/00; C07H 1/06; C07H 19/073
[52] U.S. Cl. ........................... 536/55.3; 536/28.54
[58] Field of Search .......................... 536/28.54, 55.3

[56] References Cited

U.S. PATENT DOCUMENTS 4,921,950  5/1990  Wilson ................................ 536/28.2

FOREIGN PATENT DOCUMENTS 295090  12/1988  European Pat. Off. .

OTHER PUBLICATIONS

Ishida et al. Chemical Abstracts, vol. 119, vol. 199, p. 1059, 1993. Abstract No. 226353e; Jpn Kokai Tokkyo Koho JP 93 97847, 20 Apr. 1993.

M.M. Mansuri et al. *Journal of Medicinal Chemistry*, vol. 32, No. 2, month not available 1989, pp. 461–466.

L. Dudycz, *Nucleosides and Nucleotides*, 8 (1), pp. 35–41 (1989) Month Not Available.

H. Shiragamai et al., *J. Org. Chem.*, 1988, 53, pp. 5170–5173 Month Not Available.

C.K. Chu et al. *J. Org. Chem.*, 1989, 54, pp. 2217–2225 Month Not Available.

M. Mansuri et al. *J. Org. Chem.*, 1989, 54, pp. 4780–4785 Month Not Available.

Cristol & Rademacher, *J. Am. Chem. Soc.*, 1959, 81, pp. 1600–1602 Month Not Available.

Furukawa et al. *Chem. Pharm. Bull.*, 18, 554 (1970) Month Not Available.

Kokai No. JP 05097847-A, 1993, Ishida et al Month Not Available.

Beach et al. J. Org. Chem. 57:3887–3894, 1992 Month Not Available.

*Primary Examiner*—Gary L. Kunz
*Attorney, Agent, or Firm*—Richard P. Ryan

[57] ABSTRACT

An economical process, amenable to large-scale production, is disclosed for the preparation of 2',3'-didehydro-3'-deoxythymidine (d4T) from 5-methyluridine. The process employs a novel, 5'-,acyl-2'α-halo-3'α-alkanesulfonylthymidine intermediate as well as a highly efficient and practical deprotection, isolation and purification procedure for the d4T product.

13 Claims, No Drawings

PREPARATION OF 2',3'-DIDEHYDRO-3'-DEOXYTHYMIDINE FROM 5-METHYLURIDINE

CROSS-REFERENCE TO RELATED APPLICATIONS

This is a continuation-in-part application of U.S. Ser. No. 08/153,058, filed Nov. 15, 1993 now abandoned, combined with U.S. Ser. No. 08/152,778 also filed Nov. 15, 1993 now abandoned.

BACKGROUND OF THE INVENTION

The present invention concerns a process suitable for large-scale manufacture of the anti-HIV agent, d4T. This process uses 5-methyluridine as the starting material.

The compound d4T (2',3'-didehydro-3'-deoxythymidine) has been approved for use in the treatment of AIDS. The drug has been named stavudine by USAN and is marketed as ZERIT.™ To date, d4T has been made from an expensive starting material, thymidine. Alternative methods of making this antiviral agent have been explored in order to find a more cost-effective process that would lead to a more economical method of preparing the large-scale amounts of d4T needed for a commercial drug. In this regard, not only is the expense of starting materials and reagents considered but process steps, processing time, materials handling, as well as ecological impact and health and safety concerns must also be taken into account.

Four main methods have been previously used for the transformation of a less expensive ribonucleoside, 5-methyluridine, (5-MU) to d4T:

(1) the Corey-Winter thermal decomposition of a cyclic thionocarbonate derivative of 5-MU with trialkyl phosphite. See L. Dudycz, *Nucleosides and Nucleotides*, 8 (1), 35–41 (1989);

(2) the Eastwood reaction in which the cyclic orthoester of 5-MU fragments to yield the corresponding d4T derivatives. See H. Shiragamai et al, *J. Org. Chem.*, 1988, 53, 5170–5173;

(3) the reductive elimination of a 2',3'-bisxanthate derivative of 5-MU using tributyltin hydride. See C. K. Chu et al, *J. Org. Chem.*, 1989, 54, 2217–2225; and (4) zinc reductive elimination of cis-2'-halo-3'-carboxylic esters to yield 2',3'-olefinic nucleosides. See M. Mansuri et al, *J. Org. Chem.*, 1989, 54, 4780–4785.

These methods have certain drawbacks. The major problem with (2) and (4) is significant cleavage of the nucleobond leading to generation of thymine as a difficult-to-remove by-product. Among other shortcomings, methods (1) and (3) both require selective 5'-OH group pre-protection.

The zinc reduction of vicinal bromo-tosylates to olefins is disclosed in Cristol & Rademacher, *J. Am. Chem. Soc.*, 1959, 81, 1600–1602.

Zinc reduction of a 2'-bromo-3'-methanesulfonyl ester has been used to prepare 2',3'-dideoxy-2',3'-didehydrouridine derivatives. See Ishida, et al, Kokai No. JP 05097847-A, 5 [1993].

Furukawa et al, describe the production of a 2',3'-dideoxyuridine via Pd hydrogenation of a 2'-bromo-2'-deoxy-3'-mesyluridine derivative in *Chem. Pharm. Bull.*, 18, 554 (1970). This process, however, will not result in isolation of a product with a 2',3'-double bond as in d4T.

Of less significance is the disclosure of Wilson in U.S. Pat. No. 4,921,950 covering the preparation of AZT starting with D-xylose. The starting material, intermediates, and product are not the same as for the instant process.

In sum, none of the foregoing references teach or make obvious the economical d4T process of the present invention that will provide efficient and lower cost production of d4T on a large-scale.

SUMMARY OF THE INVENTION

This invention is a more economical process for producing d4T starting with 5-methyluridine instead of the more expensive starting material, thymidine. This process also incorporates various modifications in selection of reaction sequence and the handling, processing and purification of reactants and products resulting in making the process particularly useful for adaption to large-scale manufacture. A particularly useful intermediate, a cis-2'α-halo-3'α-sulfonate ester derivative of thymidine, is also disclosed for use in this process.

DETAILED DESCRIPTION OF THE INVENTION

In its broadest aspect, the invention is a less expensive process, amenable to large-scale manufacture, for producing d4T. The process begins with 5-methyluridine (5-MU) and proceeds via a novel cis-2'α-halo-2'-deoxy-3'α-sulfonate ester derivative of 5-MU having generic formula (V).

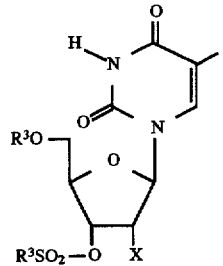

In V, $R^5$ can be hydrogen or a hydroxyl-protecting group; $R^3$ can be $C_{1-6}$ alkyl, $C_{6-30}$ aryl, C1-6 alkoxy or $C_{6-30}$ aryloxy; and X can be Cl, Br or I. By "hydroxyl-protecting group" is meant a moiety that protects the 5'-oxygen from participation in certain reactions where insulation from reaction is desired, and then subsequently the oxygen-linked-protecting group moiety can be readily converted back to an hydroxyl group. Preferred hydroxyl-protecting groups that can be used are trialkylsilyl and alkoxycarbonyl groups as well as alkyl or aryl carboxylic ester groups having $C_{1-6}$ alkyl or $C_{6-30}$ aryl residues. For use of (V) in the instant process, benzoyl is the preferred $R^5$ moiety. $R^3$ is methyl and X is bromo.

In a more narrow aspect, the invention deals with the production of d4T via a practical, economic process that can be adapted to the large-scale manufacture of d4T. In its entirety the process begins with 5-MU (formula X) and proceeds according to the reactions shown in Scheme I.

As set forth in Scheme I, the d4T process involves the following chemical reactions:

(a) The production of 2',3',5'-tri-O-mesyl-5-methyluridine (IX) from 5-MU; improvements in this step involve the use of a polar solvent, such as acetone, and about 2 to 4 equivalents of an organic base that is stronger than pyridine but weaker than triethylamine. Useful organic bases are those such as the picolines, the lutidines, and preferably N-methylmorpholine; in effect, bases with pk values between 5.5 and 8.0. The reaction proceeds at warm temperatures such as room temperature to about 65° C. and is complete within about 0.5 to 2.0 hours.

(b) The production of di-mesylated 2,2'-anhydro-5-methyluridine (VIII) by treatment of (IX) with a strong hydroxide solution such as 6N NaOH.

(c) Displacement of the 5'-mesyl group by reaction of (VIII) with benzoate anion in DMF to give the 5'-benzoate ester intermediate (VII). Potassium and sodium benzoate are preferred reagents.

(d) Halogenation using an acetyl halide in methanol or an hydrohalic acid in acetic acid, gives an intermediate of generic structure (V). Specifically, treatment of (VII) with HBr/HOAc provides the novel cis-2'α-bromo-3'α-mesyl intermediate (VI).

(e) Reductive elimination of (VI) with a metallic reducing agent, preferably zinc or a zinc-couple such as Zn-Cu, yields the 5-benzoate ester of d4T (III). The advantage of this specific reductive elimination is that it proceeds cleanly in high yield with little or no cleavage of thymine which is difficult-to-separate from product.

(f) The 5'-benzoate ester intermediate (III) is deprotected cleanly in a facile reaction with n-butylamine. The addition of N-methylpyrrolidinone (NMPO) in butyl acetate allows isolation of the d4T.NMPO solvate (II) from the reaction mixture. This isolation via the NMPO solvate effectively eliminates contaminants which are difficult to separate from product, particularly on a large scale.

(g) The solvate (II) is desolvated by heating in isopropanol to give d4T in high yield and purity.

The present invention comprises not only the total reaction sequence as shown in Scheme I but also the production of d4T from the novel formula (VI) intermediate, and the isolation/purification of product via the d4T.NMPO solvate II as separable and discrete processes in themselves.

For commercial, large-scale production of d4T from 5-MU, it is advantageous to have a reaction sequence that is reducible to a minimum number of processing steps and intermediate isolations and/or purifications. In this regard, the basic reactions of Scheme I can be arranged in several sequences leading to d4T, as shown in Scheme 2. Another aspect of the present invention is selection of a synthetic sequence that maximizes the efficiency in large-scale production by allowing the combination of reactions as well as minimal isolation and/or purification of intermediates in the process steps. After study and experimentation, the following novel process has been developed and is summarized in Scheme 3.

The Scheme 3 process comprises the following steps:

(a) The mesylation of the 2',3' and 5' hydroxy groups of 5-MU by reaction with mesyl chloride in the presence of an organic base such as the lutidines, picolines, or preferably N-methylmorpholine; followed by treatment with aqueous hydroxide to give the 2,2'-anhydrothymidine derivative (VIII).

(b) Benzoate anion displacement of the 5'-mesyl group and subsequent hydrobromination to give the 5'-benzoyl-2'α-bromo-3'α-methylthymidine compound (VI) followed by reductive elimination of (VI) with reducing metals, preferably zinc or a zinc-copper couple, to provide the 5-benzoate ester of d4T (III).

(c) Deprotecting the 5'-hydroxy position of (III) by reaction with butylamine followed by treatment with N-methylpyrrolidinone in butyl acetate to precipitate a d4T.N-methylpyrrolidinone solvate (II) that is isolated by filtration from the reaction mixture.

(d) Generation of high purity d4T (I) in good yield by desolvation of the d4T.NMPO solvate (II) by warming it in alcoholic medium, preferably isopropanol.

In this process, the removal of the benzoyl (or another acyl group) from the 5'-position is done with n-butylamine. Such a reaction of an amine with an ester is not used often because required reaction conditions generally are more extreme (especially temperature and reaction time). The reaction by-products are also problematic because they are often difficult to separate from the product.

Another problem complicating removal of a 5'-acyl group from d4T is the high solubility of d4T in water and alcohols. Water and alcohols or mixtures of these are the typical solvents that 5'-deprotection reactions utilize. Prior art syntheses of d4T generally use sodium methoxide in methanol to achieve 5'-deprotection. Since aqueous extractions will not separate by-product sodium salts from the water-soluble product, strong acid resins are then usually employed for removal of sodium salts generated in the deprotection reaction. This is followed by removal of the methanol and subsequent isolation of d4T from a methylene chloride mixture.

For large-scale manufacture, the use of strong acid resins and replacement of the methanol medium with methylene chloride are objectionable operations in and of themselves without taking into account other unfavorable aspects of these isolation and purification procedures.

By way of contrast, the new deprotection/isolation/purification procedure of the present invention involves:

stirring the 5'-acyl d4T intermediate in butylamine at about 70° C. for about 6 hours;

adding NMPO and butyl acetate;

removing excess butylamine (and some of the butyl acetate) in vacuo;

cooling to about −10° C. and filtering the precipitate, which is washed with cold butyl acetate and, if desired, oven dried in vacuo at about 50° C.

Not only is this procedure more efficient, but it eliminates the problem caused by contaminating the water soluble d4T with hard-to-remove inorganic salts.

This more efficient process for making d4T from 5-MU offers advantages not only in yield and purity of product but in adaptability for large-scale production due to the process steps fashioned and the reagents and reaction conditions that they employ.

In sum, the new, lower cost process for producing d4T and related analogs is amenable to large-scale use by virtue of its selection of process steps and reagents, reaction conditions, and separation/purification features that result in an efficient process minimizing troublesome impurities and product degradation as well as providing a high yield and purity of product without generation of wastes that are either toxic or produced in large volume.

DESCRIPTION OF SPECIFIC EMBODIMENTS

The improved process of this invention is illustrated in greater detail by the following examples directed to preferred embodiments of the process steps described supra. These examples should not be construed as limiting the scope of the present invention in any way. Some of the exemplified compounds are not actually isolated but are carried on in the process steps of this invention. Other examples that follow show a previously utilized procedure for the sake of comparison with the procedure designed for use in the present process.

A. Compound IX

Example 1

2',3',5'-Tris(methanesulfonyl)-5-methyluridine a. Pyridine procedure

To a stirred mixture of 5-methyluridine (12.8 g, 50 mmol) in pyridine (75 ml) at 0° C. was added methanesulfonyl chloride (17.4 ml, 225 mmol). The reaction mixture was stirred at 0° C. for five hours then poured into ice-water (500 ml) with stirring. Tris(methanesulfonyl)-5-methyluridine (IX) precipitated and the mixture was stirred for 5 min. The solid product was collected by filtration and washed with water (3×200 ml) and dried. Yield 21.6 g, 89%.

$^1$H-NMR (DMSO-d$_6$) δ1.77 (s, 3H), 3.24 (s, 3H), 3.34 (s, 3H), 3.36 (s, 3H), 4.47–4.60 (m, 2H), 5.33 (m, 1H), 5.54 (m, 1H), 5.97 (d, J=4.5 Hz, 1H), 7.56 (s, 1H), 11.56 (s, 1H).

b. N-Methylmorpholine procedure

N-Methylmorpholine (29.6 mL, 266 mmoles) was added to a slurry of 5-methyluridine hemihydrate (15.64 g, 58.5 mmoles) in acetone (68 mL) and the resulting mixture was cooled to 5° C. A solution of methanesulfonyl chloride (20.1 mL, 255 mmoles) in acetone (30 mL) was added over 45 minutes, causing the reaction temperature to rise to 45°–50° C. After stirring an additional 1.4 hours the N-methylmorpholine hydrochloride was removed by filtration and the cake was washed with acetone (2×30 mL). The combined filtrate and washes were then added to water (1 L) at 10°–15° C. After stirring for 1.1 hours the white precipitate was filtered, washed with water (2×75 mL), and dried under vacuum. Yield 27.95 g (97%).

B. Compound VIII

Example 2

3',5'-Di-O-methanesulfonyl-2,2'-anhydro-5-methyluridine

To the stirred mixture of 5-methyluridine (200 g, 0.748 mol) in acetone (400 ml) at 5° C. was added N-methylmorpholine (NMM, 380 ml, 3.46 mol). A solution of mesyl chloride (256 ml, 3.31 mol) in acetone (40 ml) was then added, allowing the reaction temperature to reach 65° C. in ten minutes. Maintain the pot temperature at 60°–65° C. throughout most of the addition. The reaction mixture was then stirred for two hours until the temperature gradually reached 25° C. The NMM-HCl salt was filtered and the cake washed with acetone (3×350 ml). The filtrate and acetone rinse were combined and water (400 ml) was added. The pH of the reaction mixture was adjusted to 8.8–9.0 with 6N NaOH using an automatic titrator while warming the temperature to 50°–55° C. The pot was stirred for one hour at 50° C. after it had maintained pH 9 for approximately 30 minutes. The resulting thick slurry was then cooled to 2°–5° C. and filtered. The cake was washed with 3×600 ml of water and dried to give intermediate product (VIII), 266 g (89.7%).

$^1$H-NMR (DMSO-d$_6$) δ1.80 (s, 3H), 3.16 (s, 3H), 3.41 (s, 3H), 4.16 (m, 1H), 4.34 (m, 1H), 4.70 (m, 1H), 5.44 (s, 1H), 5.62 (d, J=5.7 Hz, 1 H), 6.40 (d, J=5.7 Hz, 1H), 7.80 (s, 1H).

C. Compound VII

Example 3

5'-Benzoyl-3'-methanesulfonyl-2,2'-anhydro-5-methyluridine

To a stirred slurry of sodium benzoate (10 g, 69.3 mmol) in acetamide (50 g) at 115° C. was added 2',3',5'-tris(methanesulfonyl)-5-methyluridine (IX, 10 g, 20.3 mmol). The reaction mixture was stirred at 115° C. for 65 min. and then poured into ice water (2 L). The mixture was stirred at 0° C. for 15 min. The white solid was filtered, washed with water (2×50 ml) and dried to give compound (VII), 7.76 g (90%).

$^1$H-NMR (DMSO-d$_6$) δ1.74 (s, 3H), 3.44 (s, 3H), 4.16–4.33 (m, 2H), 4.78 (m, 1H), 5.63 (s, 1H), 5.68 (d, J=5.7 Hz, 1H), 6.45 (d, J=5.7 Hz, 1H), 7.79 (s, 1H), 7.47–7.89 (m, 5H).

D. Compound VI

Example 4

5'-Benzoyl-3'α-methanesulfonyl-2'α-bromo-thymidine a. From 5'-Benzoyl-3'-methanesulfonyl-2,2'-anhydro-5-methyluridine (VIII)

To a stirred mixture of 5'-benzoyl-3'-methanesulfonyl-2,2'-anhydro-5-methyluridine (VIII) (4.0 g, 9.5 mmol) in ethyl acetate (100 ml) and methanol (10 ml) was added acetyl bromide (5 ml, 67.7 mmol). The reaction mixture was refluxed for one hour and then cooled. The reaction mixture was transferred to a separatory funnel. Ethyl acetate (150 ml) was added. The solution was washed with saturated sodium bicarbonate (100 ml) followed by brine (100 ml). The organic layer was separated and dried over MgSO$_4$. Removal of solvent gave the solid product (VI). Yield, 4.86 g, 100%.

$^1$H-NMR (DMSO-d$_6$) δ1.63 (s, 3H), 3.37 (s, 3H), 4.50–4.55 (m, 1H), 4.60–4.64 (m, 2H), 5.09 (t, J=6.0 Hz, 1H), 5.47 (m, 1H), 6.14 (d, J=7.2 Hz, 1), 7.49 (s, 1H), 7.50–8.04 (m, 5H), 11.56 (s, 1H).

b. From 2',3',5'-Tris(methanesulfonyl)-5-methyluridine (IX)

To a slurry of powdered sodium benzoate (3.5 g, 24.3 mmol), in DMAc (25 ml) at 90° C. was added tris(methanesulfonyl)-5-methyluridine (IX, 5.0 g, 10.2 mmol). The reaction was stirred for 5.5 hours at 90° C. HBr/HOAc (30–32%, 5 ml, 25.1 mmol) was added and the reaction was stirred for one hour. After cooling, the reaction mixture was diluted with 500 ml ethyl acetate and 100 ml water. The phases were separated and the organic phase was washed with 100 ml water, 50 ml brine and dried over MgSO$_4$. Removal of solvent afforded compound (VIa), 5.01 g (98%).

E. Compound III

Example 5

5'-Benzoyl-2',3'-didehydro-3'-deoxythymidine (5'-benzoyl-d4T)

a. From 5'-Benzoyl-3'α-methanesulfonyl-2'α-bromo-thymidine (VI)

5'-Benzoyl-3'-methanesulfonyl-2'-bromo-5-methyluridine (VI, 6.0 g, 11.9 mmoles) was suspended in a mixture of ethyl acetate (112.5 mL) and methanol (37.5 mmoles). To this slurry was added acetic acid (0.68 mL) and zinc dust (1.36 g) at 18° C. After 3.5 hours the excess zinc was removed by filtration and the cake was washed with a 3:1 mixture of ethyl acetate/methanol (2×30 mL). The solvent was removed under vacuum and more 3:1 ethyl acetate/methanol (20 mL) was added. To this slurry was then added water (225 mL). The resulting slurry was filtered and the product was washed with water and dried. Yield 3.8 g (97%) of intermediate product (III).

$^1$H-NMR (DMSO-d$_6$) δ1.35 (s, 3H), 4.41–4.48 (m, 2H), 5.10 (m, 1H), 6.04 (d, J=5.8 Hz, 1H), 6.53 (d, J=5.8 Hz, 1H), 6.80 (s, 1H), 7.10 (s, 1H), 7.51–7.95 (m, 5H), 11.37 (s, 1H).

b. From 3',5'-Bis(methanesulfonyl)-2,2'-anhydro-5-methyluridine (VIII)

To the stirred mixture of 3',5'-bis(methanesulfonyl)-2,2'-anhydro-5-methyluridine (VIII, 200 g, 0.505 mol) in DMF (600 ml) at 95°–97° C. was added powdered sodium benzoate (79.56 g, 0.552 mol) portion-wise in one hour. The resulting mixture was stirred for an additional five hours at 95°–97° C. After cooling to 80° C., acetyl bromide (3.8 ml) was added followed by HBr/HOAc (30–32%, 120 ml, 0.605 mol). The reaction was stirred at 90° C. for one to two hours then cooled to 0°–5° C. Zinc dust (42.8 g, 0.655 mol) was added portion-wise and the reaction was allowed to exotherm to 50°–55° C. The reaction was then stirred at 18°–25° C. for one hour. Bromoacetic acid (21.0 g) was added and the mixture stirred for two to three hours to consume excess zinc metal. To the resulting clear solution was next added water (1.5–2.0 L) and the pot was cooled to 2° C. The slurry was filtered and the cake was washed with ice water (6×600 ml) and then cold IPA (−10° C., 400 ml). The cake was dried to constant weight, 136.9 g (87.9%).

c. From 2',3',5'-Tris(methanesulfonyl)-5-methyluridine (IX)

To a slurry of powdered sodium benzoate (3.5 g, 24.3 mmol) in DMF (25 ml) at 90° C. was added tris (methanesulfonyl)-5-methyluridine (IX, 5.0 g, 10.2 mmol). The reaction was stirred for 5.5 hours at 90° C. HBr/HOAc (30–32%, 5 ml, 25.1 mmol) was added and the reaction was stirred for one hour. The reaction mixture was cooled to 25° C. and zinc dust (2.0 g, 30.6 mmol) was added. The reaction was stirred for 30 minutes. The excess zinc was removed by filtration and washed with 2×100 ml methanol. To the filtrate was added 100 ml ice-cold water. The resulting slurry was stirred at 0° C. for 30 minutes and then filtered, dried to give 5'-benzoyl-d4T, 2.34 g (71%).

F. Compound II

Example 6

2',3'-Didehydro-3'-deoxythymidine-N-methylpyrrolidinone solvate

To n-butylamine (133 ml) was added 5'-benzoyl-d4T (III, 70.0 g). The reaction was heated at 70° C. for six hours. After cooling to 20°–25° C., N-methylpyrrolidinone (NMPO, 41.3 ml) and n-butyl acetate (350 ml) were added. Excess n-butylamine (~112.4 ml) along with 175 ml of n-butyl acetate was removed via vacuum distillation at 50° C. The resulting slurry was cooled to 20°–25° C. over one hour and stirred for 30 minutes. The slurry was then cooled to −10° to −15° C. and stirred for 1.5 hours. The cake was filtered and washed with 2×50 ml cold (−10° to −15° C.) n-butyl acetate and dried to give d4T.NMPO solvate (II), 59.0 g (85.6%).

G. Compound I

Example 7

2',3'-Didehydro-3'-deoxythymidine (d4T)

a. Methoxide procedure

To a stirred slurry of 5'-benzoyl-d4T (III) (2.4 g, 7.31 mmol) in methanol (24 ml) was added sodium methoxide solution (4.8 mL, 25%, 21 mmol). The resulting solution was stirred at room temperature for 3 hours. The reaction mixture was neutralized with strong acid resin (Dowex 50×8–200, prewashed with methanol) to pH 4. The resin was filtered and the cake was washed with methanol (2×0ml). Removal of methanol gave a wet solid to which methylene chloride (10 ml) was added. The resulting mixture was stirred for 30 min. and then the d4T product (I) was collected by filtration, washed with methylene chloride (2×5ml) and dried. Yield 1.29 g, 79%.

$^1$H-NMR (DMSO-$d_6$) δ1.71 (s, 3H), 3.59 (m, 4.76 (m, 1H), 4.76 (m, 1H), 502 (s, 1H), 5.89 (d, J=5.7 Hz, 1H), 6.38 (d, J=5.7 Hz, 1H), 6.80 (s, 1H), 7.63 (s, 1H), 11.27 (s, 1H).

b. d4T.NMPO solvate procedure

To 500 ml of isopropanol was added 50.0 g d4T.NMPO (II), 5.0 g Dicalite, 5.0 g Darco KB. The mixture was heated to reflux and then filtered hot through a bed of Dicalite. The filter cake was rinsed with 150 ml hot isopropanol. The filtrate and rinse were combined and vacuum concentrated to a final volume of 200 ml. The concentrated mixture was heated to reflux to give a solution and then cooled slowly to form product slurry at 50° C. The slurry was then cooled to 0° C. and held for 30 minutes. The cake was filtered, washed with cold (0° C.) isopropanol and dried to give d4T (I), 30.5 g (87.9%).

SCHEME I

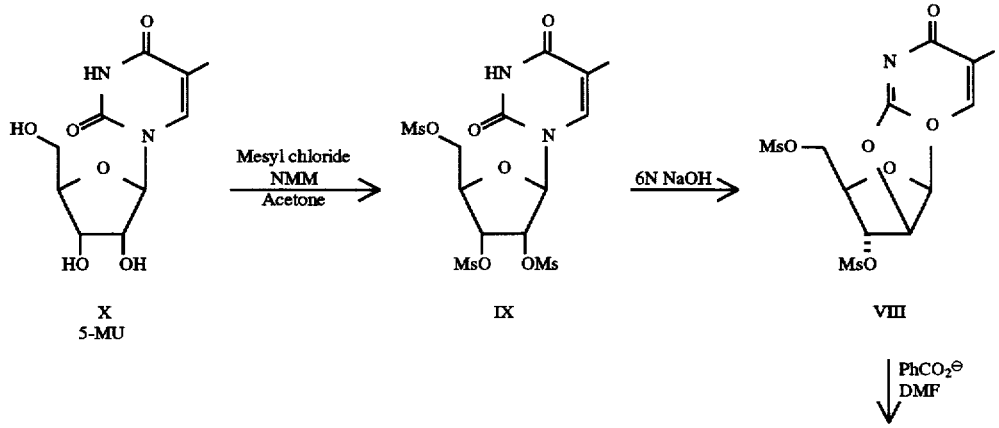

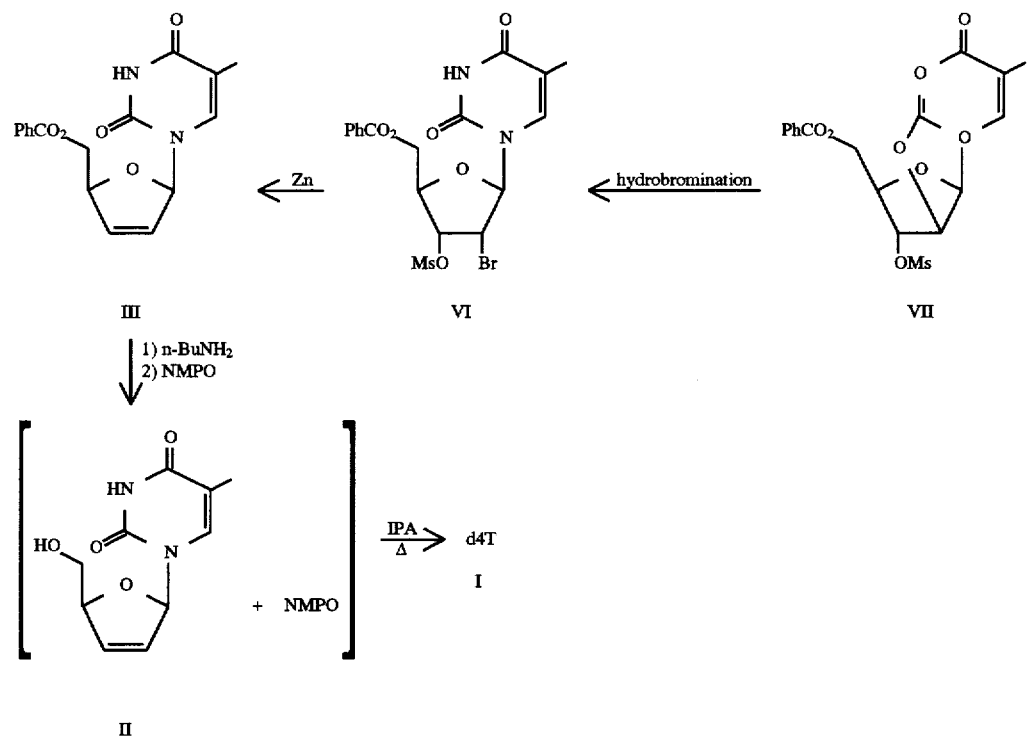
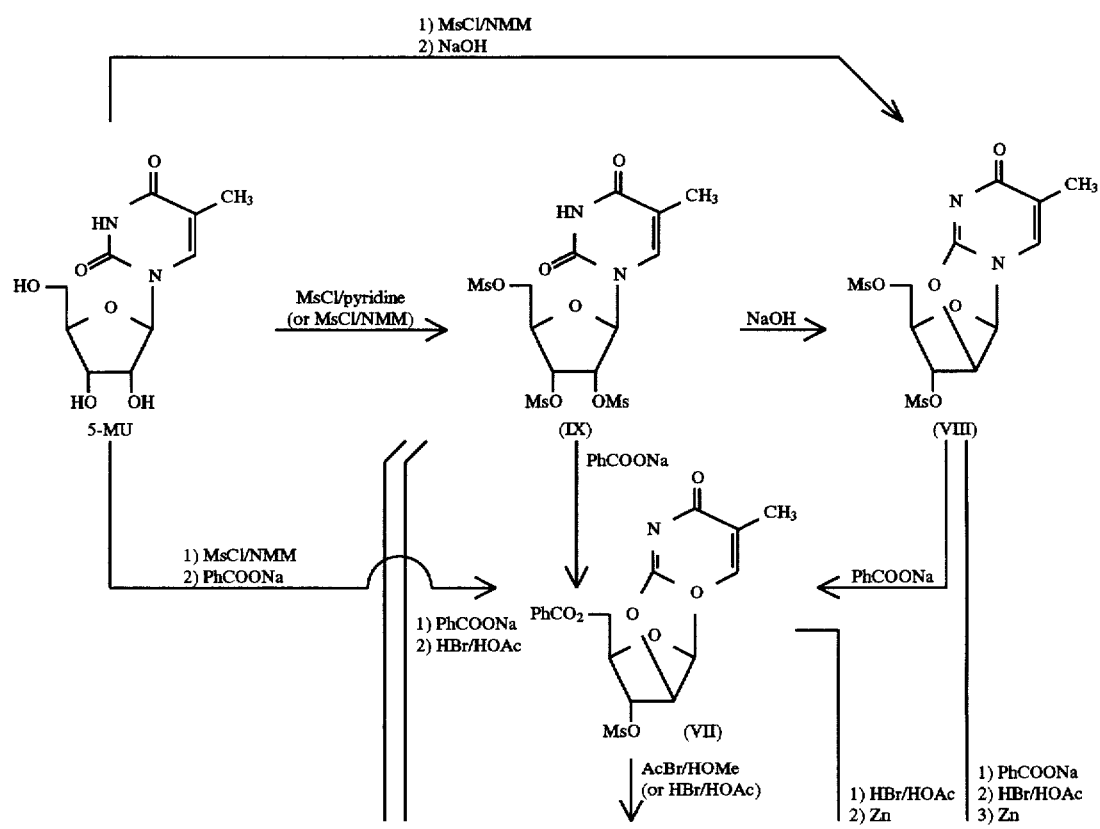

-continued
Scheme 2
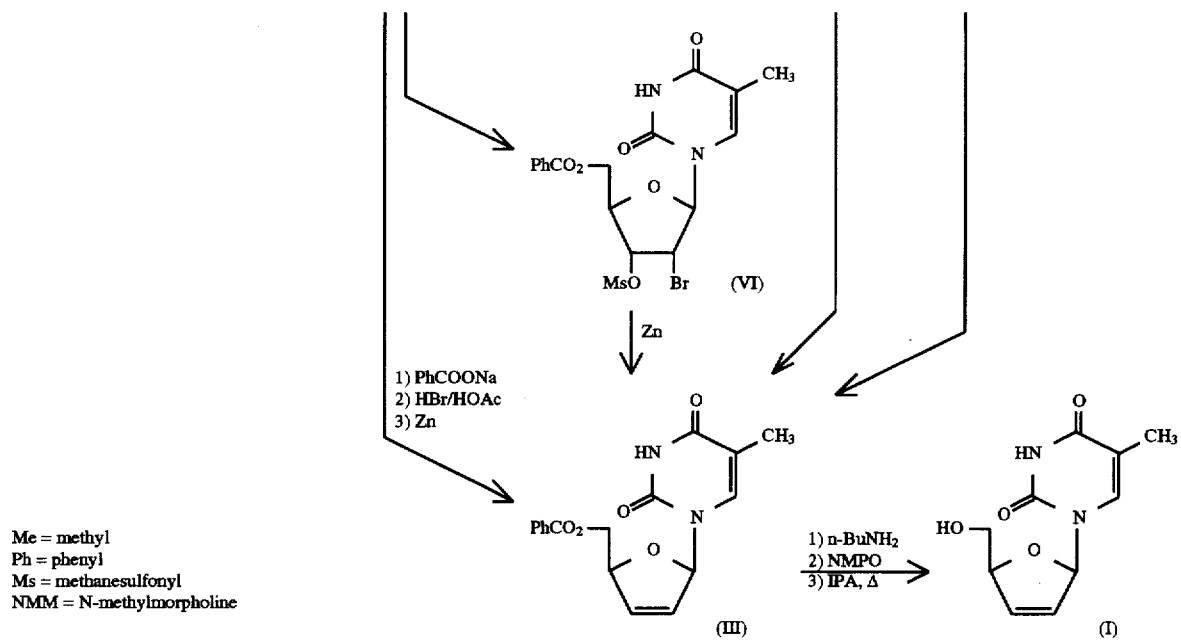
Me = methyl
Ph = phenyl
Ms = methanesulfonyl
NMM = N-methylmorpholine
Scheme 3
D4T PROCESS FROM 5-METHYLURIDINE
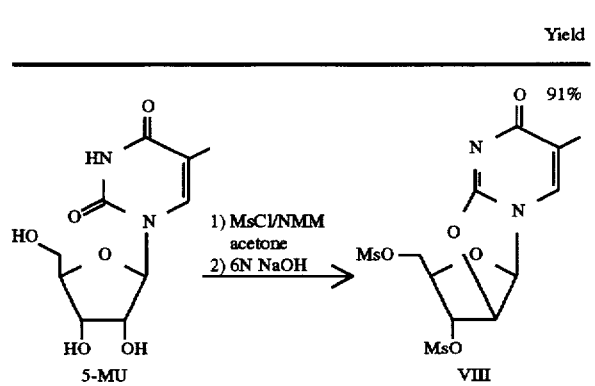
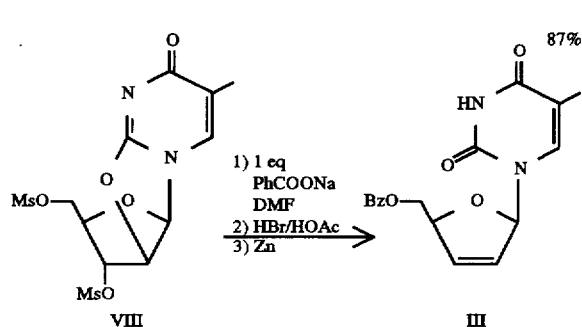
-continued
Scheme 3
D4T PROCESS FROM 5-METHYLURIDINE
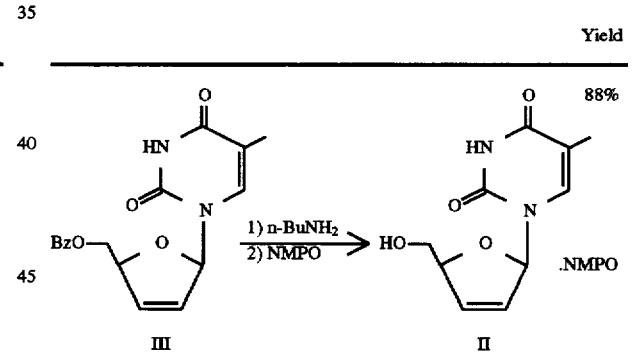
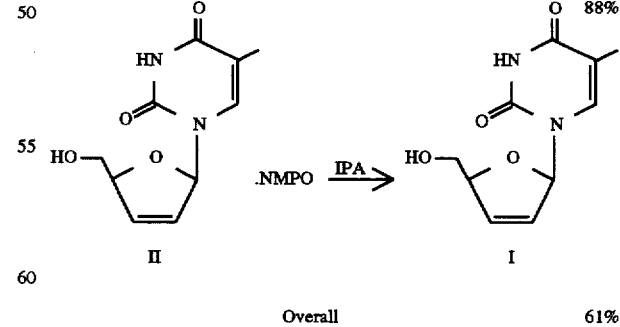
Overall 61%

We claim:

1. A process for producing 2',3'-didehydro-3'-deoxythymidine (d4T) comprising the steps of:

(a) reacting 5-methyluridine (X) with mesyl chloride in the

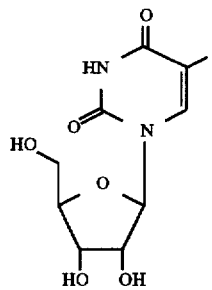

X presence of an organic base with a $pk_a$ value between about 5.5 and 8.0 to mesylate the 2',3' and 5' hydroxy groups, followed by treatment with hydroxide to provide the 2,2'-anhydro compound (VIII);

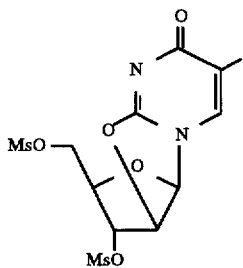

VIII (b) displacing the 5'-mesyl group with benzoate anion followed by hydrobromination to give the 5'-benzoyl-2'-bromo compound (VI);

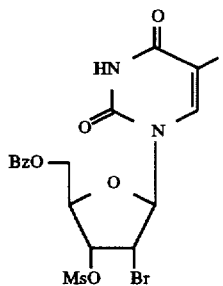

VI (c) reducing the compound of Formula VI in the presence of zinc to provide the 5'-benzoate ester of d4T (III);

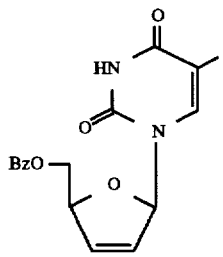

III (d) treating (III) with butylamine followed by N-methylpyrrolidinone and butyl acetate to give the d4T.NMPO solvate (II);

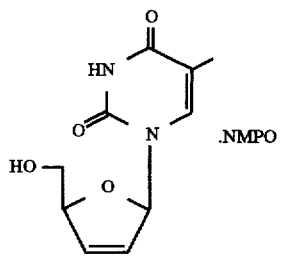

II and (e) generation of d4T product (I) by desolvating the d4T.NMPO solvate (II) in alcoholic medium.

2. The process of claim 1 wherein the organic base in step (a) is N-methylmorpholine.

3. The process of claim 1 wherein the hydrobromination of step (b) is accomplished with HBr in acetic acid.

4. A process for purification of crude d4T comprising 1) the formation and isolation of an N-methylpyrrolidinone solvate of d4T (II) from a process reaction mixture and 2) the generation of purified d4T by desolvation of the solvate (II) by heating in an alcoholic medium.

5. The purification process of claim 4 wherein the alcoholic medium for decomposition of the solvate (II) is isopropanol.

6. An intermediate of Formula V, useful in nucleoside derivative synthesis,

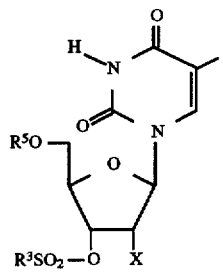

V wherein $R^5$ is hydrogen or a hydroxyl-protecting group; $R^3$ is $C_{1-6}$alkyl, $C_{1-6}$alkoxy, $C_{6-30}$aryl, or $C_{6-30}$aryloxy; and X is chloro, bromo, or iodo.

7. The intermediate of claim 6 wherein $R^5$ is benzoyl, $R^3$ is methyl and X is bromo.

8. A process for producing d4T by (a) treating a compound of Formula V, wherein $R^3$ is selected from $C_{1-6}$alkyl and $C_{6-30}$aryl, and $R^5$ is selected from $C_{1-6}$alkylcarbonyl and $C_{6-30}$arylcarbonyl and X is bromo,

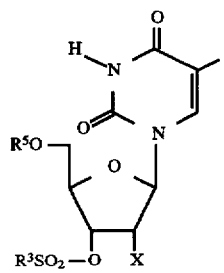

V with zinc metal to give compound (III) wherein R is $C_{1-6}$alkyl or $C_{6-30}$aryl;

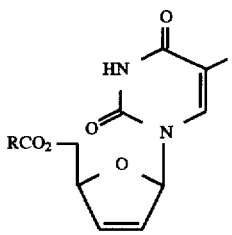

III

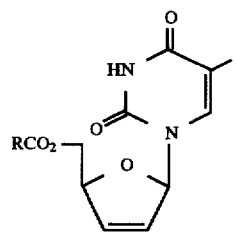

III comprising the zinc reduction of a compound of Formula V

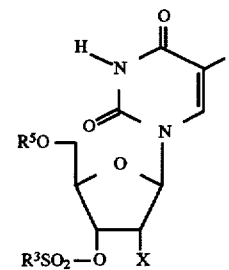

V (b) treating compound (III) with a primary or secondary alkylamine followed by N-methylpyrrolidinone to give the d4T.NMPO solvate (II); and (c) generating d4T product by desolvating the d4T.NMPO solvate (II) in alcoholic medium.

9. The process of claim 8 wherein the alcoholic medium of step 3) is isopropanol.

10. The process of claim 8 wherein $R^3$ is methyl and $R^5$ is $C_{6-30}$arylcarbonyl.

11. The process of claim 8 wherein the alkylamine of step (b) is n-butylamine.

12. A process for preparing a compound of Formula III, wherein R is $C_{1-6}$alkyl or $C_{6-30}$aryl;

wherein $R^3$ is $C_{1-6}$alkyl or $C_{6-30}$aryl, $R^5$ is $C_{1-6}$alkylcarbonyl or $C_{6-30}$arylcarbonyl, and X is chloro, bromo or iodo.

13. The process of claim 12 wherein compound (V) is defined by $R^3$ being methyl, $R^5$ being benzoyl, and X being bromo.

* * * * *